US011510291B2

(12) United States Patent
Horrod et al.

(10) Patent No.: US 11,510,291 B2
(45) Date of Patent: Nov. 22, 2022

(54) TUBULAR HEATING ELEMENT SUITABLE FOR AEROSOLIZABLE MATERIAL

(71) Applicant: Nicoventures Trading Limited, London (GB)

(72) Inventors: Martin Daniel Horrod, Cambridge (GB); Julian Darryn White, Cambridge (GB)

(73) Assignee: Nicoventures Trading Limited, London (GB)

( * ) Notice: Subject to any disclaimer, the term of this patent is extended or adjusted under 35 U.S.C. 154(b) by 309 days.

(21) Appl. No.: 15/733,326

(22) PCT Filed: Dec. 18, 2018

(86) PCT No.: PCT/EP2018/085684
§ 371 (c)(1),
(2) Date: Jun. 26, 2020

(87) PCT Pub. No.: WO2019/129552
PCT Pub. Date: Jul. 4, 2019

(65) Prior Publication Data

US 2020/0324065 A1 Oct. 15, 2020

(30) Foreign Application Priority Data

Dec. 28, 2017 (GB) ...................................... 1722183

(51) Int. Cl.
*A61M 15/06* (2006.01)
*H05B 6/10* (2006.01)
(Continued)

(52) U.S. Cl.
CPC ........... *H05B 6/108* (2013.01); *A24F 40/465* (2020.01); *A61M 15/06* (2013.01); *H05B 6/105* (2013.01);
(Continued)

(58) Field of Classification Search
CPC .. H05B 6/108; H05B 6/105; H05B 2203/021; H05B 6/10; A24F 40/465; A61M 15/06;
(Continued)

(56) References Cited

U.S. PATENT DOCUMENTS

2008/0038363 A1* 2/2008 Zaffaroni ............. A61M 11/041 424/502
2015/0272219 A1* 10/2015 Hatrick ................. A24F 40/465 131/328
(Continued)

FOREIGN PATENT DOCUMENTS

CN 103783668 5/2014
CN 204949521 1/2016
(Continued)

OTHER PUBLICATIONS

International Search Report and Written Opinion, Application No. PCT/EP2018/085684, dated Jun. 3, 2019, 23 pages.

*Primary Examiner* — Truc T Nguyen
(74) *Attorney, Agent, or Firm* — Patterson Thuente, P.A

(57) ABSTRACT

Disclosed is a tubular heating element for use in an apparatus for heating aerosolizable material to volatilize at least one component of the aerosolizable material. The tubular heating element further includes heating material layer that is heatable by penetration with a varying magnetic field on a tubular support. The tubular heating element has a wall thickness of no more than one millimeter. Further, the tubular heating element can include a protective layer. The heating layer includes a ferromagnetic material based on cobalt or nickel.

20 Claims, 2 Drawing Sheets

(51) Int. Cl.
*A24F 40/465* (2020.01)
*A61M 11/04* (2006.01)

(52) U.S. Cl.
CPC ... *A61M 11/042* (2014.02); *A61M 2205/3368* (2013.01); *A61M 2205/3653* (2013.01); *A61M 2205/8206* (2013.01); *H05B 2203/021* (2013.01)

(58) Field of Classification Search
CPC ........ A61M 11/042; A61M 2205/3368; A61M 2205/3653; A61M 2205/8206
See application file for complete search history.

(56) References Cited

U.S. PATENT DOCUMENTS

| | | | | |
|---|---|---|---|---|
| 2016/0120221 | A1 | 5/2016 | Mironov | |
| 2017/0027233 | A1 | 2/2017 | Mironov | |
| 2017/0055583 | A1* | 3/2017 | Blandino | H05B 6/06 |
| 2017/0079326 | A1 | 3/2017 | Mironov | |
| 2017/0079330 | A1 | 3/2017 | Mironov | |
| 2017/0086508 | A1 | 3/2017 | Mironov | |
| 2017/0105452 | A1 | 4/2017 | Mironov | |
| 2017/0156403 | A1* | 6/2017 | Gill | A24F 40/60 |
| 2019/0364973 | A1* | 12/2019 | Kaufman | A24F 40/465 |
| 2020/0324065 | A1* | 10/2020 | Horrod | A61M 15/06 |
| 2021/0298363 | A1* | 9/2021 | Daugherty | A61M 15/0081 |
| 2022/0076867 | A1* | 3/2022 | Parker | H01F 7/02 |

FOREIGN PATENT DOCUMENTS

| | | |
|---|---|---|
| EP | 0703735 | 4/1996 |
| JP | 2005 221626 | 8/2005 |
| WO | WO 95/27411 | 10/1995 |
| WO | WO 2008/129662 | 10/2008 |
| WO | WO 2016/075436 | 5/2016 |
| WO | WO 2017/001818 | 1/2017 |
| WO | WO 2017/068094 | 4/2017 |
| WO | WO 2017/068099 | 4/2017 |
| WO | WO 2018/178095 | 10/2018 |

* cited by examiner

TUBULAR HEATING ELEMENT SUITABLE FOR AEROSOLIZABLE MATERIAL

PRIORITY CLAIM

The present application is a National Phase entry of PCT Application No. PCT/EP2018/085684, filed Dec. 18, 2018, which claims priority from GB Patent Application No. 1722183.9, filed Dec. 28, 2017, each of which is hereby fully incorporated herein by reference.

TECHNICAL FIELD

The present disclosure relates to tubular heating elements for use in apparatus for heating aerosolizable material to volatilize at least one component of the aerosolizable material, to apparatus for heating aerosolizable material to volatilize at least one component of the aerosolizable material, and to systems comprising such apparatus and an article comprising the aerosolizable material.

BACKGROUND

Smoking articles such as cigarettes, cigars and the like burn tobacco during use to create tobacco smoke. Attempts have been made to provide alternatives to these articles by creating products that release compounds without combusting. Examples of such products are so-called "heat not burn" products or tobacco heating devices or products, which release compounds by heating, but not burning, material. The material may be, for example, tobacco or other non-tobacco products, which may or may not contain nicotine.

SUMMARY

A first aspect of the present disclosure provides a tubular heating element for use in apparatus for heating aerosolizable material to volatilize at least one component of the aerosolizable material, wherein the tubular heating element comprises heating material that is heatable by penetration with a varying magnetic field, and wherein the tubular heating element has a wall thickness of no more than 1 millimeter.

In an exemplary embodiment, the wall thickness is no more than 0.5 millimeters. In an exemplary embodiment, the wall thickness is no more than 0.3 millimeters. In an exemplary embodiment, the wall thickness is at least 0.05 millimeters.

In an exemplary embodiment, an outside diameter or dimension of the tubular heating element is no more than 5 millimeters. In an exemplary embodiment, the outside diameter or dimension is no more than 2.4 millimeters. In an exemplary embodiment, the outside diameter or dimension is at least 0.3 millimeters.

In an exemplary embodiment, an inside diameter or dimension of the tubular heating element is at least 0.1 millimeters. In an exemplary embodiment, the inside diameter or dimension is at least 0.19 millimeters. In an exemplary embodiment, the inside diameter or dimension is no more than 2.1 millimeters.

In an exemplary embodiment, the tubular heating element comprises a heat resistant support and a coating on the support, and the coating comprises the heating material. In an exemplary embodiment, the coating is located radially outwards of the support.

A second aspect of the present disclosure provides a tubular heating element for use in apparatus for heating aerosolizable material to volatilize at least one component of the aerosolizable material, wherein the tubular heating element comprises a heat resistant support and a coating on the support, wherein the coating comprises heating material that is heatable by penetration with a varying magnetic field, and wherein the coating is located radially outwards of the support.

In an exemplary embodiment of the tubular heating element of the first or second aspect, the coating has a thickness of no more than 50 microns. In an exemplary embodiment, the coating has a thickness of no more than 20 microns.

In an exemplary embodiment of the tubular heating element of the first or second aspect, the coating is annular.

In an exemplary embodiment of the tubular heating element of the first or second aspect, the heating material of the coating is a ferromagnetic material. In an exemplary embodiment, the ferromagnetic material comprises nickel or cobalt.

In an exemplary embodiment of the tubular heating element of the first or second aspect, the tubular heating element is free from a coating comprising heating material radially inwards of the heat resistant support.

In an exemplary embodiment of the tubular heating element of the first or second aspect, the support comprises one or more materials selected from the group consisting of: a metal, a metal alloy, a ceramics material, and a plastics material.

In an exemplary embodiment of the tubular heating element of the first or second aspect, the tubular heating element comprises a heat resistant protective coating, and the coating comprising the heating material is located between the support and the heat resistant protective coating.

In an exemplary embodiment, the coating comprising the heating material is encapsulated. In an exemplary embodiment, the heat resistant protective coating and the support together encapsulate the coating comprising the heating material. In an exemplary embodiment, the heat resistant protective coating encapsulates the support and the coating comprising the heating material.

In an exemplary embodiment of the tubular heating element of the first or second aspect, the heat resistant protective coating comprises one or more materials selected from the group consisting of: a ceramics material, metal nitride, titanium nitride, and diamond.

In an exemplary embodiment of the tubular heating element of the first or second aspect, the heat resistant protective coating has a thickness of no more than 50 microns. In an exemplary embodiment, the heat resistant protective coating has a thickness of no more than 20 microns.

In an exemplary embodiment of the tubular heating element of the first or second aspect, the tubular heating element comprises a needle.

A third aspect of the present disclosure provides apparatus for heating aerosolizable material to volatilize at least one component of the aerosolizable material, the apparatus comprising: a heating zone for receiving one or more articles comprising aerosolizable material; a heating element comprising heating material that is heatable by penetration with a varying magnetic field to heat the heating zone, wherein the heating element is encircled by the heating zone; and a magnetic field generator for generating varying magnetic fields that penetrate respective longitudinal portions of the heating element in use, wherein the magnetic field generator comprises a plurality of flat spiral coils of electrically-conductive material arranged sequentially and in respective planes along a longitudinal axis of the heating zone.

In an exemplary embodiment, the heating element extends parallel to, or coaxially with, a longitudinal axis of the heating zone.

In an exemplary embodiment, the heating element is tubular.

In an exemplary embodiment, the heating element comprises a needle.

In an exemplary embodiment, the heating element comprises a heat resistant support and a coating on the support, and the coating comprises the heating material. In an exemplary embodiment, the heating material of the coating is a ferromagnetic material. In an exemplary embodiment, the ferromagnetic material comprises nickel or cobalt. In an exemplary embodiment, the coating is located radially outwards of the support.

In an exemplary embodiment, the heating element of the apparatus comprises the tubular heating element of the first aspect of the present disclosure or the tubular heating element of the second aspect of the present disclosure.

In an exemplary embodiment, the apparatus comprises a body that holds the heating element in position relative to the heating zone and defines at least one air inlet through which air is able to enter the heating zone in use.

In an exemplary embodiment, the heating element is removable from the apparatus. In an exemplary embodiment, a combination of the heating element and the body is removable from the apparatus.

In an exemplary embodiment, the planes are substantially parallel to one another.

In an exemplary embodiment, the heating zone extends through a hole in each of the plurality of flat spiral coils.

In an exemplary embodiment, the apparatus comprises an elongate support for supporting an article comprising aerosolizable material in the holes in the flat spiral coils. In an exemplary embodiment, the elongate support is tubular and encircles the heating zone. In an exemplary embodiment, elongate support is magnetically impermeable and/or electrically non-conductive.

In an exemplary embodiment, the apparatus comprises a controller for controlling operation of at least one of the flat spiral coils independently of at least one other of the flat spiral coils.

In an exemplary embodiment, the apparatus is a tobacco heating product.

In an exemplary embodiment of the tubular heating element of the first or second aspect or the apparatus of the third aspect, the heating material comprises one or more materials selected from the group consisting of: an electrically-conductive material, a magnetic material, and a magnetic electrically-conductive material. In an exemplary embodiment, the heating material comprises a metal or a metal alloy. In an exemplary embodiment, the heating material comprises one or more materials selected from the group consisting of: aluminum, gold, iron, nickel, cobalt, conductive carbon, graphite, steel, plain-carbon steel, mild steel, stainless steel, ferritic stainless steel, copper, and bronze.

A fourth aspect of the present disclosure provides a system for heating aerosolizable material to volatilize at least one component of the aerosolizable material, the system comprising: the apparatus of the third aspect of the present disclosure; and the article comprising aerosolizable material and for locating in the heating zone of the apparatus.

In an exemplary embodiment, the aerosolizable material comprises tobacco and/or one or more humectants.

BRIEF DESCRIPTION OF THE DRAWINGS

Embodiments of the disclosure will now be described, by way of example only, with reference to the accompanying drawings, in which.

DETAILED DESCRIPTION

Figure 1:
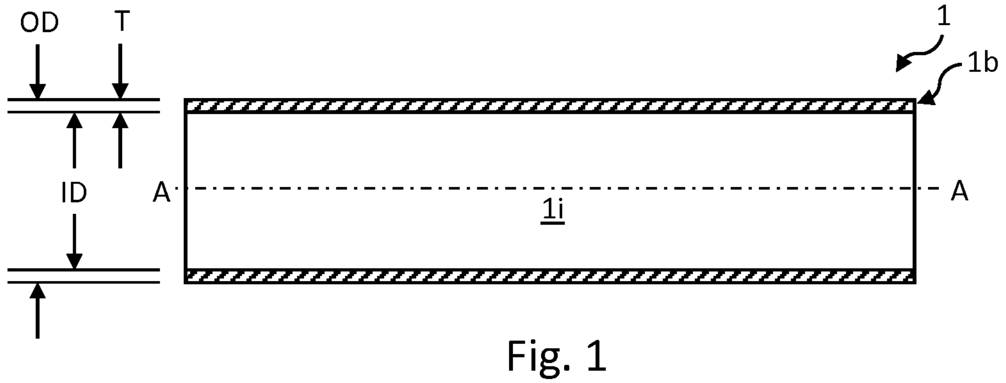
FIG. 1 shows a schematic cross-sectional side view of an example of a tubular heating element for use in apparatus for heating aerosolizable material to volatilize at least one component of the aerosolizable material.

As used herein, the term “aerosolizable material” includes materials that provide volatilized components upon heating, typically in the form of vapor or an aerosol. “aerosolizable material” may be a non-tobacco-containing material or a tobacco-containing material. “aerosolizable material” may, for example, include one or more of tobacco per se, tobacco derivatives, expanded tobacco, reconstituted tobacco, tobacco extract, homogenized tobacco or tobacco substitutes. The aerosolizable material can be in the form of ground tobacco, cut rag tobacco, extruded tobacco, reconstituted tobacco, reconstituted aerosolizable material, liquid, gel, gelled sheet, powder, or agglomerates, or the like. “Aerosolizable A material” also may include other, non-tobacco, products, which, depending on the product, may or may not contain nicotine. “Aerosolizable A material” may comprise one or more humectants, such as glycerol or propylene glycol.

As used herein, the term “heating material” or “heater material” refers to material that is heatable by penetration with a varying magnetic field.

Induction heating is a process in which an electrically-conductive object is heated by penetrating the object with a varying magnetic field. The process is described by Faraday’s law of induction and Ohm’s law. An induction heater may comprise an electromagnet and a device for passing a varying electrical current, such as an alternating current, through the electromagnet. When the electromagnet and the object to be heated are suitably relatively positioned so that the resultant varying magnetic field produced by the electromagnet penetrates the object, one or more eddy currents are generated inside the object. The object has a resistance to the flow of electrical currents. Therefore, when such eddy currents are generated in the object, their flow against the electrical resistance of the object causes the object to be heated. This process is called Joule, ohmic, or resistive heating. An object that is capable of being inductively heated is known as a susceptor.

It has been found that, when the susceptor is in the form of a closed electrical circuit, magnetic coupling between the susceptor and the electromagnet in use is enhanced, which results in greater or improved Joule heating.

Magnetic hysteresis heating is a process in which an object made of a magnetic material is heated by penetrating the object with a varying magnetic field. A magnetic material can be considered to comprise many atomic-scale magnets, or magnetic dipoles. When a magnetic field penetrates such material, the magnetic dipoles align with the magnetic field. Therefore, when a varying magnetic field, such as an alternating magnetic field, for example as produced by an electromagnet, penetrates the magnetic material, the orientation of the magnetic dipoles changes with the varying applied magnetic field. Such magnetic dipole reorientation causes heat to be generated in the magnetic material.

When an object is both electrically-conductive and magnetic, penetrating the object with a varying magnetic field can cause both Joule heating and magnetic hysteresis heating in the object. Moreover, the use of magnetic material can strengthen the magnetic field, which can intensify the Joule and magnetic hysteresis heating.

In each of the above processes, as heat is generated inside the object itself, rather than by an external heat source by heat conduction, a rapid temperature rise in the object and more uniform heat distribution can be achieved, particularly through selection of suitable object material and geometry, and suitable varying magnetic field magnitude and orientation relative to the object. Moreover, as induction heating and magnetic hysteresis heating do not require a physical connection to be provided between the source of the varying magnetic field and the object, design freedom and control over the heating profile may be greater, and cost may be lower.

Referring to FIG. 1, there is shown a schematic cross-sectional side view of an example of a tubular heating element according to an embodiment of the disclosure. The tubular heating element 1 is for use in apparatus for heating aerosolizable material to volatilize at least one component of the aerosolizable material, such as the apparatus 100 shown in FIG. 4 and described below.

The tubular heating element 1 comprises heating material **1*b* that is heatable by penetration with a varying magnetic field. In some embodiments, such as this, the tubular heating element 1 consists of the heating material 1*b*. The heating material 1*b*** may be any of those described herein, such as stainless steel.

In this embodiment, the heating element **1*b* is substantially cylindrical with a substantially circular cross section, but in other embodiments the heating element 1*b* may have an oval or elliptical cross section. In some embodiments, the heating element 1*b*** may have a polygonal, quadrilateral, rectangular, square, triangular, star-shaped, or irregular cross section, for example.

In this embodiment, the heating element **1*b* is elongate and has a longitudinal axis A-A. In other embodiments, the heating element 1*b* may not be elongate. In some such other embodiments, the heating element 1*b* still has an axial direction A-A that is perpendicular to the cross section of the heating element 1*b***.

The heating element **1*b* has a hollow inner region 1*i*, and a wall thickness T that is measured between inside and outside diameters (or dimensions perpendicular to the axial direction A-A) ID, OD of the heating element 1*b*. The tubular heating element 1** of this embodiment has a wall thickness T of about 0.13 millimeters. In other embodiments, the wall thickness T may be other than this. In some embodiments, the wall thickness T is no more than 1 millimeter, such as no more than 0.5 millimeters, and for example no more than 0.3 millimeters. In some embodiments, the wall thickness T is at least 0.05 millimeters. In one embodiment, the wall thickness T is between 0.05 millimeters and 0.3 millimeters.

The tubular heating element 1 of this embodiment has an outside diameter or dimension OD of about 1.65 millimeters. In other embodiments, the outside diameter or dimension OD may be other than this. In some embodiments, the outside diameter or dimension OD is no more than 5 millimeters, such as no more than 2.4 millimeters. In some embodiments, the outside diameter or dimension OD is at least 0.3 millimeters. In one embodiment, the outside diameter or dimension OD is between 0.3 millimeters and 5 millimeters.

The tubular heating element 1 of this embodiment has an inside diameter or dimension ID of about 1.39 millimeters. In other embodiments, the inside diameter or dimension ID may be other than this. In some embodiments, the inside diameter or dimension ID is at least 0.1 millimeters, such as at least 0.19 millimeters. In some embodiments, the inside diameter or dimension ID is no more than 2.1 millimeters. In one embodiment, the inside diameter or dimension ID is between 0.1 millimeters and 2.1 millimeters.

Figure 2:
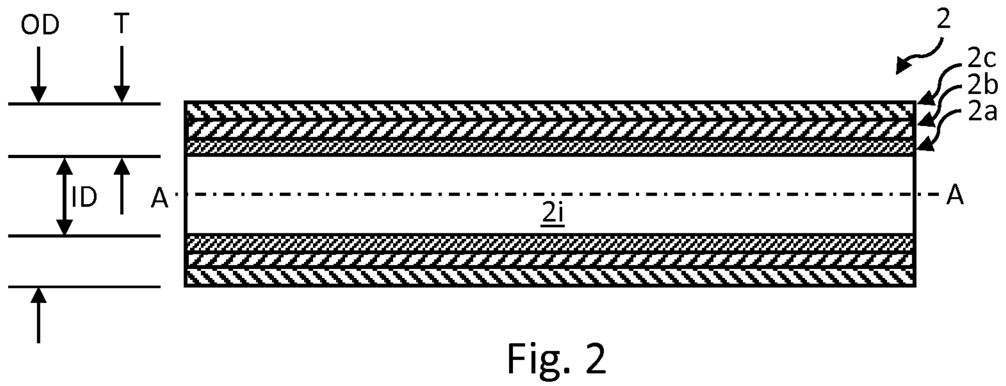
FIG. 2 shows a schematic cross-sectional side view of an example of another tubular heating element for use in apparatus for heating aerosolizable material to volatilize at least one component of the aerosolizable material.

FIG. 2 shows a schematic cross-sectional side view of an example of another tubular heating element according to an embodiment of the disclosure. The tubular heating element 2 is again for use in apparatus for heating aerosolizable material to volatilize at least one component of the aerosolizable material, such as the apparatus 100 shown in FIG. 4 and described below.

The heating element 2 of FIG. 2 comprises a heat resistant support **2*a*, a coating 2*b* comprising heating material located on the support 2*a*, and a heat resistant protective coating 2*c* arranged so that the coating 2*b* comprising heating material is located between the support 2*a* and the heat resistant protective coating 2*c***. The heating material again is heatable by penetration with a varying magnetic field.

In this embodiment, the heating element 2 is substantially cylindrical with a substantially circular cross section, but in other embodiments the heating element 2 may have an oval or elliptical cross section. In some embodiments, the heating element 2 may have a polygonal, quadrilateral, rectangular, square, triangular, star-shaped, or irregular cross section, for example.

In this embodiment, the heating element 2 is elongate and has a longitudinal axis A-A. In other embodiments, the heating element 2 may not be elongate. In some such other embodiments, the heating element 2 still has an axial direction A-A that is perpendicular to the cross section of the heating element 2.

The heating element 2 has a hollow inner region **2*i*, and a wall thickness T that is measured between inside and outside diameters (or dimensions perpendicular to the axial direction A-A) ID, OD of the heating element 2**. In some embodiments, the wall thickness T is no more than 1 millimeter, such as no more than 0.5 millimeters or no more than 0.3 millimeters. In some embodiments, the outside diameter or dimension OD is between 0.3 millimeters and 5 millimeters. In some embodiments, the inside diameter or dimension ID is between 0.1 millimeters and 2.1 millimeters.

The heat resistant support 2*a* of this embodiment is tubular. The heat resistant support 2*a* of this embodiment comprises steel, and more specifically stainless steel. However, in other embodiments, the heat resistant support 2*a* may for example comprise one or more materials selected from the group consisting of: a metal, a metal alloy, a ceramics material, and a plastics material. For example, in some embodiments, the heat resistant support 2*a* may comprise steel, mild steel, aluminum, copper, or a high temperature polymer such as polyether ether ketone (PEEK) or Kapton.

The coating 2*b* comprising heating material is a layer or coating 2*b* on the support 2*a*. In this embodiment, the coating 2*b* comprises cobalt. However, in other embodiments, the coating 2*b* could comprise a heating material other than cobalt, such as nickel. In some embodiments, however, the heating material of the coating 2*b* is a ferromagnetic material.

In this embodiment, the coating 2*b* is located radially outwards of the support 2*a*. That is, the coating 2*b* is on an outer side of the heat resistant support 2*a*. Moreover, in this embodiment, a radially inward facing side of the heat resistant support 2*a* is free from a coating comprising heating material. In other embodiments, a coating comprising heating material (such as a ferromagnetic material, e.g. cobalt or nickel) may be provided radially inwards of the heat resistant support 2*a* in addition to, or alternatively to, radially outwards of the heat resistant support 2*a*. However, if such a coating is provided radially inwardly in addition to radially outwardly, the thermal mass of the heating element 2 may be increased, which can reduce the rate at which the heating element 2 is heatable by a given varying magnetic field in use.

In this embodiment, the coating 2*b* is annular and encircles the support 2*a*. In other embodiments, the coating 2*b* may be non-annular or only partially annular, and thus not fully encircle the support 2*a*.

In this embodiment, the coating 2*b* has a thickness of about 10 microns. However, in other embodiments, the coating 2*b* may have a different thickness, such as a thickness of no more than 50 microns or no more than 20 microns. For example, when the ferromagnetic material of the coating is nickel, the coating 2*b* may have a thickness of about 15 microns. The coating 2*b* may be a film or a plating.

The heat resistant protective coating 2*c* is provided on the coating 2*b* comprising heating material. More specifically, the coating 2*b* is located between the support 2*a* and the heat resistant protective coating 2*c*. The heat resistant protective coating 2*c* of this embodiment comprises titanium nitride. However, in other embodiments, the heat resistant protective coating 2*c* may for example comprise one or more materials selected from the group consisting of: a ceramics material, metal nitride, titanium nitride, and diamond. In this embodiment, the heat resistant protective coating 2*c* has a thickness of about 10 microns. However, in other embodiments, the heat resistant protective coating 2*c* may have a different thickness, such as a thickness of no more than 50 microns or no more than 20 microns.

In this embodiment, the heat resistant protective coating 2*c* is located radially outwards of the heat resistant support 2*a* and the coating 2*b* comprising heating material. That is, the heat resistant protective coating 2*c* is on an outer side of the coating 2*b*. Moreover, in this embodiment, a radially inward facing side of the heat resistant support 2*a* is free from a heat resistant protective coating 2*c*. However, in other embodiments, a heat resistant protective coating 2*c* may be provided radially inwards of the heat resistant support 2*a* in addition to, or alternatively to, radially outwards of the heat resistant support 2*a*. However, again, if a heat resistant protective coating 2*c* is provided radially inwardly in addition to radially outwardly, the thermal mass of the heating element 2 may be increased.

In this embodiment, the heat resistant protective coating 2*c* is annular and encircles the support 2*a* and the coating 2*b* comprising heating material. In other embodiments, the heat resistant protective coating 2*c* may be non-annular or only partially annular, and thus not fully encircle the support 2*a* and the coating 2*b* comprising heating material.

The coating 2*b* comprising heating material coating may become increasingly susceptible to oxidation as it increases in temperature. This can increase heat loss due to radiation by increasing the relative emissivity (Er) relative to the unoxidized surface, enhancing the rate at which energy is lost through radiation. If the energy radiated ends up being lost to the environment, then such radiation can reduce the system energy efficiency. Oxidation can also reduce the resistance of the coating 2*b* to chemical corrosion, which could result in shortening the service life of the heating element 2. Therefore, in some embodiments, such as that of FIG. 2, the coating 2*b* comprising heating material is coated with a heat resistant protective coating 2*c*, such as one of those described above. Titanium nitride can be applied using physical vapor deposition, for example. Other example heat resistant protective coatings are a ceramics material, metal nitride, and diamond. In some embodiments, the heat resistant protective coating 2*c* can be provided in a different way, such as by chemically treating the coating 2*c* comprising heating material to encourage growth of a protective film over the coating 2*b* comprising heating material, or formation of a protective oxide layer using a process such as anodization. In addition to protecting the underlying coating 2*b* from oxidation, the heat resistant protective coating 2*c* may also help to physically protect the coating 2*b* comprising heating material from mechanical wear.

In some embodiments that are variations to the illustrated embodiment, the coating 2*b* comprising heating material is encapsulated. In some embodiments, the heat resistant protective coating 2*c* and the support 2*a* together encapsulate the coating 2*b* comprising heating material. In some other embodiments, the heat resistant protective coating 2*c* encapsulates the support 2*a* and the coating 2*b* comprising heating material.

In some embodiments, the heat resistant protective coating 2*c* may have low or no electrical conductivity, so as not to (or not to significantly) result in the induction of electric currents in the heat resistant protective coating 2*c* rather than the coating 2*b* comprising heating material.

Figure 3:
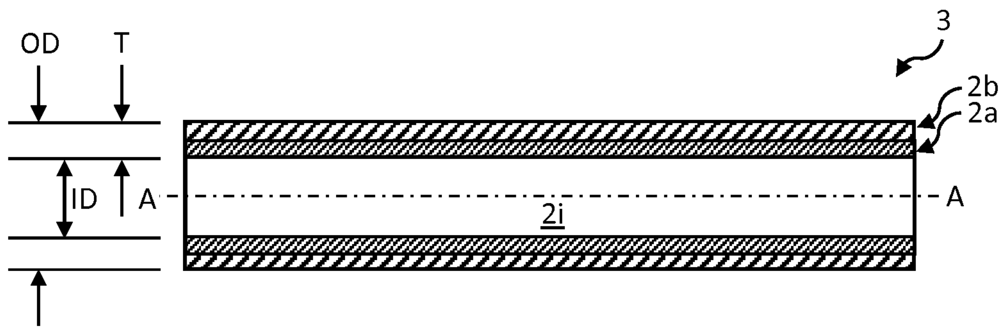
FIG. 3 shows a schematic cross-sectional side view of an example of another tubular heating element for use in apparatus for heating aerosolizable material to volatilize at least one component of the aerosolizable material.

In some embodiments, the heat resistant protective coating 2*c* is omitted. For example, FIG. 3 shows a schematic cross-sectional side view of an example of another tubular heating element according to an embodiment of the disclosure. The tubular heating element 3 of FIG. 3 is again for use in apparatus for heating aerosolizable material to volatilize at least one component of the aerosolizable material, such as the apparatus 100 shown in FIG. 4 and described below.

The tubular heating element 3 of FIG. 3 is identical to that of FIG. 2 (and so like features have like reference numerals), except that the heat resistant protective coating 2*c* is omitted. Any of the herein-described variations to the tubular heating element 2 of FIG. 2 may be made to the tubular heating element 3 of FIG. 3 to form further embodiments. In some embodiments, the wall thickness T of the tubular heating element 3 is no more than 1 millimeter, such as no more than 0.5 millimeters or no more than 0.3 millimeters. In some embodiments, the outside diameter or dimension OD of the tubular heating element 3 is between 0.3 millimeters and 5 millimeters. In some embodiments, the inside diameter or dimension ID of the tubular heating element 3 is between 0.1 millimeters and 2.1 millimeters In some embodiments, the tubular heating element 1, 2, 3 is a needle.

Dimensions for tubular heating elements of some example embodiments of the present disclosure are given in the table below:

| OD (mm) | ID (mm) | T (mm) |
|---|---|---|
| 0.305 | 0.190 | 0.058 |
| 0.457 | 0.305 | 0.076 |
| 0.510 | 0.305 | 0.103 |
| 0.560 | 0.381 | 0.090 |
| 0.635 | 0.406 | 0.115 |
| 0.710 | 0.510 | 0.100 |
| 0.810 | 0.63.5 | 0.088 |
| 0.890 | 0.660 | 0.115 |
| 10.67 | 0.810 | 0.129 |
| 1.240 | 0.910 | 0.165 |
| 1.470 | 1.140 | 0.165 |
| 1.650 | 1.390 | 0.130 |
| 1.828 | 1.473 | 0.178 |
| 2.108 | 1.828 | 0.140 |
| 2.388 | 2.058 | 0.165 |

In some embodiments, the OD may vary by +/−0.13 mm from the relevant figure given in the table above. In some embodiments, the wall thickness T may vary by +/−15% from the relevant figure given in the table above. In some embodiments, a tubular heating element with the dimensions given in one of the rows above may comprise or consist of stainless steel.

During induction heating, energy from a varying magnetic field is transferred to the heating material of the tubular heating element 1, 2, 3, causing the temperature of the heating material to rise. In order that the heating material heats up as efficiently as possible, the transfer of energy to the heating material should be as lossy as possible, so that the energy transferred is quickly converted to heat. Reducing the thermal mass of the tubular heating element 1, 2, 3 increases the change in temperature for a given energy input. By providing tubular heating element 1, 2, 3 with a wall thickness of no more than 1 millimeter, the thermal mass of the tubular heating element 1, 2, 3 can be kept low.

For conductive (and magnetizable) media there is a characteristic depth (the "skin depth") into which the electromagnetic field is able to penetrate. The present inventors have found that, if a surface of a tubular heating element 2, 3, such as a surface facing the magnetic field generator in use, is coated with a thin coating **2*b* (such as a few microns) comprising heating material (such as nickel or cobalt or another ferromagnetic material), then the coating 2*b* need only be very thin to effect the same absorption as a thicker mild steel plate. The coating 2*b* could for example be applied by a chemical plating method, an electro-chemical plating method, or by vacuum evaporation. If nickel is used, the coating 2*b* or layer thickness may be as little as 15 microns. Moreover, if cobalt is used, the coating 2*b* or layer thickness can be reduced to approximately 10 microns. A thickness of one or more skin depths should help to ensure that a majority of the available energy is directed into the heating element 2, 3**. A thickness of around two skin depths may be optimal in some embodiments.

In some embodiments, the heating material coating **2*b*** comprises cobalt. Cobalt has a Curie point temperature (around 1,120 to 1,127 degrees Celsius) that is well above the normal operating temperatures of heating elements of embodiments of the present disclosure. The Curie point temperature, or Curie Temperature, is the temperature at which certain magnetic materials undergo a sharp change in their magnetic properties. It is understood that the Curie point temperature is the temperature below which there is spontaneous magnetization in the absence of an externally applied magnetic field, and above which the material is paramagnetic. For example, the Curie point temperature is the magnetic transformation temperature of a ferromagnetic material between its ferromagnetic and paramagnetic phase. When such a magnetic material reaches its Curie point temperature, its magnetic permeability reduces or ceases, and the ability of the material to be heated by penetration with a varying magnetic field also reduces or ceases. That is, it may not be possible to heat the material above its Curie point temperature by magnetic hysteresis heating. As cobalt has a Curie point temperature well above the normal operating temperatures of heating elements of embodiments of the present disclosure, the effect of the Curie point temperature will be much less pronounced (or even, in some embodiments, indiscernible) during normal operation than if, say, nickel were to be used instead.

The support **2*a* on which the coating 2*b* or layer comprising heating material is provided need not interact with the applied varying magnetic field to generate heat in the support 2*a*. That is, the support 2*a* need not itself be heatable by penetration with a varying magnetic field. All the support 2*a* need be able to achieve is supporting the heating material coating 2*b* while resisting the heat generated therein. Accordingly, the support 2*a*** can be made from any suitable heat resistant material, such as those described herein.

It will therefore be appreciated that heating elements of example embodiments of the present disclosure enable efficient transfer of energy from a varying magnetic field into the heating element while retaining the benefits of relatively low cost, ease of material availability, and ease of forming during manufacture.

Figure 4:
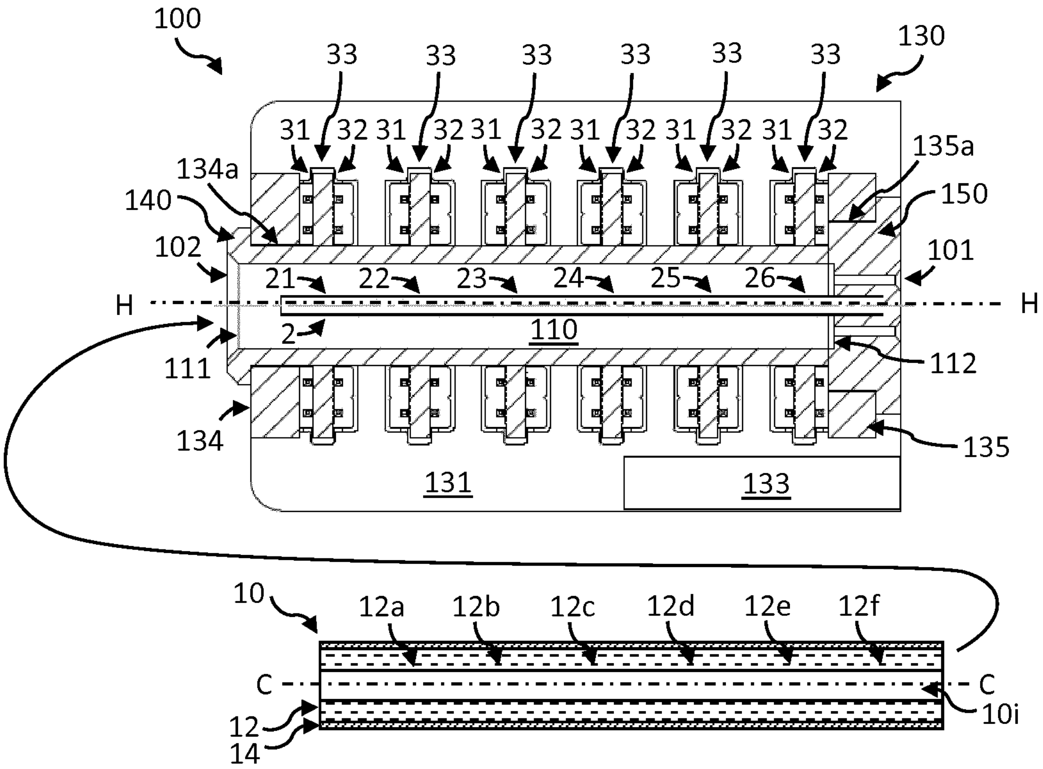
FIG. 4 shows a schematic cross-sectional side view of an example of a system comprising apparatus for heating aerosolizable material to volatilize at least one component of the aerosolizable material, and an article comprising the aerosolizable material and for locating in a heating zone of the apparatus.

Referring to FIG. 4, there is shown a schematic cross-sectional view of an example of a system according to an embodiment of the disclosure. The system 1000 comprises an article 10 comprising aerosolizable material 12, and an apparatus 100 for heating the aerosolizable material 12 to volatilize at least one component of the aerosolizable material 12. In this embodiment, the aerosolizable material 12 comprises tobacco, and the apparatus 100 is a tobacco heating product (also known in the art as a tobacco heating device or a heat-not-burn device).

In this embodiment, the aerosolizable material 12 is in the form of a hollow tube, and the article 10 comprises a cover 14 around the aerosolizable material 12. The article 10 as a whole is a hollow tube with a hollow interior **10*i*. In this embodiment, the hollow interior 10*i* is defined by the aerosolizable material 12, but in other embodiments the article 10 may comprise another component, such as an inner wrapper, that defines the hollow interior 10*i*. In some embodiments, the article 10** may be a non-hollow rod.

The cover 14 encircles the aerosolizable material 12, and helps to protect the aerosolizable material 12 from damage during transport and use of the article 10. During use, the cover 14 may also help to direct the flow of air into and through the aerosolizable material 12, and may help to direct the flow of aerosol through and out of the aerosolizable material 12. In this embodiment, the cover 14 comprises a wrapper that is wrapped around the aerosolizable material 12 so that free ends of the wrapper overlap each other. The wrapper thus forms all of, or a majority of, a circumferential outer surface of the article 10. The wrapper may be formed from paper, reconstituted tobacco, aluminum, or the like. The cover 14 also comprises an adhesive (not shown) that adheres the overlapped free ends of the wrapper to each other. The adhesive may comprise one or more of, for example, gum Arabic, natural or synthetic resins, starches, and varnish. The adhesive helps prevent the overlapped free ends of the wrapper from separating. In other embodiments, the adhesive and/or the cover 14 may be omitted. In still other embodiments, the article may take a different form to any of those discussed above. For example, in some embodiments the article 10 may include a filter for filtering aerosol generated in the article 10 in use.

Broadly speaking, the apparatus 100 comprises a heating zone 110, a heating element 2 comprising heating material that is heatable by penetration with a varying magnetic field to heat the heating zone 110, and a magnetic field generator 130 for generating varying magnetic fields that penetrate respective longitudinal portions 21, 22, 23, 24, 25, 26 of the heating element 2 in use. In this embodiment, the heating element 2 is that described herein with reference to FIG. 2. However, in other embodiments, the heating element of the apparatus 100 could take a different form, such as that described herein with reference to FIG. 1 or FIG. 3 or that of any of the variations to the heating elements 1, 2, 3 described herein. However, in some embodiments the heating element is tubular.

The heating zone 110 encircles the heating element 2. In this embodiment, the heating element 2 extends coaxially with a longitudinal axis H-H of the heating zone 110. In some other embodiments, the heating element 2 extends parallel to the longitudinal axis H-H of the heating zone 110, or perpendicular to the longitudinal axis H-H of the heating zone 110, or obliquely to the to the longitudinal axis H-H of the heating zone 110.

The heating zone 110 is for receiving one or more articles comprising aerosolizable material, such as the article 10 described above. That is, the article 10 is for locating in the heating zone 110. In this embodiment, the heating zone 110 comprises a recess for receiving the article 10. More specifically, the hollow article 10 is moveable relative to the heating zone 110 and the heating element 2 in such a way that the heating element 2 becomes located in the hollow interior 10*i* of the article 10 during insertion of the article 10. The hollow interior 10*i* of the article 10 is dimensioned to receive the heating element 2 of the apparatus 100. In embodiments in which the article 10 is a non-hollow rod, the heating element 2 may be pushed into the article 10 (such as into the aerosolizable material 12 of the article 10) during insertion of the article 10, so as to create a space in the article 10 for the heating element 2.

The article 10 may be insertable into the heating zone 110 by a user in any suitable manner, such as through a slot in a wall of the apparatus 100, or by first moving a portion of the apparatus 100, such as a mouthpiece, to access the heating zone 110. In other embodiments, the heating zone 110 may be other than a recess, such as a shelf, a surface, or a projection, and may require mechanical mating with the article 10 in order to co-operate with, or receive, the article 10. In this embodiment, the heating zone 110 is sized and shaped to accommodate the whole article 10. In other embodiments, the heating zone 110 may be dimensioned to receive only a portion of the article 10 in use.

The apparatus 100 has a plurality of air inlets 101 that fluidly connect the heating zone 110 with the exterior of the apparatus 100, and an outlet 102 for permitting volatilized material to pass from the heating zone 110 to an exterior of the apparatus 100 in use. A user may be able to inhale the volatilized component(s) of the aerosolizable material 12 by drawing the volatilized component(s) through the outlet 102. As the volatilized component(s) is/are removed from the heating zone 110, air may be drawn into the heating zone 110 via the air inlets 101 of the apparatus 100. A first end 111 of the heating zone 110 is closest to the outlet 102, and a second end 112 of the heating zone 110 is closest to the air inlets 101. In other embodiments, only a singular air inlet 101 may be provided.

Figure 5:
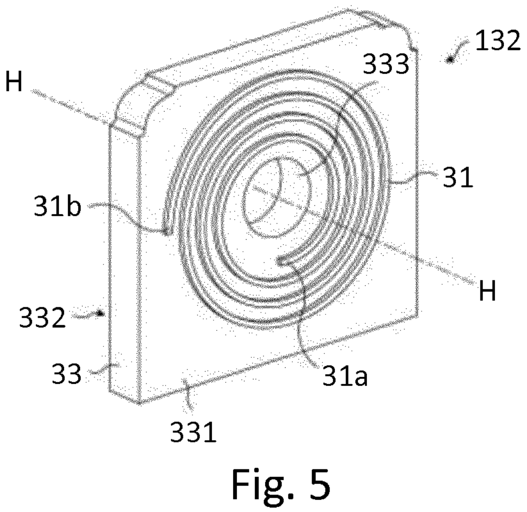
FIG. 5 shows a schematic perspective view of an induction coil arrangement of the apparatus shown in FIG. 4.

The magnetic field generator 130 comprises a plurality of flat spiral coils 31, 32 of electrically-conductive material arranged sequentially and in respective planes along the longitudinal axis H-H of the heating zone 110. More specifically, the magnetic field generator 130 of the apparatus 100 comprises a retainer 131 and a plurality of induction coil arrangements connected or attached to the retainer 131. The retainer 131 may hold the induction coil arrangements in a fixed position relative to each other, relative to the retainer 131, and relative to the heating zone 110 and heating element 2. A schematic perspective view of one of the induction coil arrangements is shown in FIG. 5.

The induction coil arrangement 132 comprises a board, panel or plate 33 and a pair of the flat spiral coils 31, 32 of electrically-conductive material, such as copper. In use, a varying (e.g. alternating) electric current is passed through each of the coils 31, 32 so as to create a varying (e.g. alternating) magnetic field that is usable to penetrate the heating element 2 to cause heating of the heating element 2.

The plate 33 has a first side 331 and an opposite second side 332. The first and second sides 331, 332 of the plate 33 face away from each other. In this embodiment, the plate 33 is substantially planar, and the first and second sides 331, 332 are major sides of the plate 33. The plate 33 should be made from a non-electrically-conductive material, such as a plastics material, so as to electrically-insulate the coils 31, 32 from each other. In this embodiment, the plate 33 is made from FR-4, which is a composite material composed of woven fiberglass cloth with an epoxy resin binder that is flame retardant, but in other embodiments other material may be used. A first 31 of the flat spiral coils of electrically-conductive material is mounted on the first side 331 of the plate 33, and a second 32 of the flat spiral coils of electrically-conductive material is mounted on the second side 332 of the plate 33. Accordingly, the plate 33 is located between the coils 31, 32.

The coils 31, 32 may be affixed to the plate 33 in any suitable way. In this embodiment, the induction coil arrangement 132 has been formed from printed circuit board (PCB), and so the first and second flat spiral coils 31, 32 have been formed by printing the electrically-conductive material onto the respective first and second sides 331, 322 of the board or plate 33 during manufacture of the PCB, and then removing (such as by etching) selective portions of the electrically-conductive material so that patterns of the electrically-conductive material in the form of the first and second flat spiral coils 31, 32 remain on the plate 33. Accordingly, the first and second flat spiral coils 31, 32 are thin films or coatings of electrically-conductive material on the plate 33.

The induction coil arrangement 132 of this embodiment therefore comprises a laminate having a first layer (comprising the first flat spiral coil 31), a second layer (comprising the second flat spiral coil 32), and an intermediate third layer (the plate 33) between the first and second layers. The plate 33 thus spaces apart the first and second layers. As the plate 33 is made of non-electrically-conductive material, the coils 31, 32 are electrically insulated from each other (other than for the electrically-conductive connector, discussed below). That is, the coils 31, 32 are out of contact with each other. In other embodiments, the coils 31, 32 may be electrically insulated from each other in a different way, such as by an air gap between the coils 31, 32. In some embodiments, the coils 31, 32 may be provided on the plate 33 in any other suitable way, such as by being pre-formed and then attached to the plate 33. In some embodiments, the plate 33 may be other than a layer of a PCB. For example, it may be a layer or sheet of material such as resin or adhesive, which may have dried, cured or solidified.

The use of coils formed from thin, printed electrically-conductive material as discussed above obviates the need for Litz wire. Litz wire is comprised of many strands of extremely thin wire gathered in a braid, in order to overcome the effects of diminishing skin depth at higher excitation frequencies. As the tracks on a PCB are thin (typically around 38 um thick for 1 Oz Cu, and around 76 um thick for 2 Oz Cu), their performance at high frequencies can be comparable to the equivalent cross-sectional area of Litz wire, yet without problems arising in relation to brittleness, shaping the Litz wire, or connecting it to other components.

The first and second flat spiral coils 31, 32 are exposed on the plate 33, which helps enable the dissipation of any heat generated in the coils 31, 32 during use. However, in other embodiments the first and second flat spiral coils 31, 32 may instead be embedded within material, such as the material that forms the plate 33, to help protect the coils 31, 32 from damage during transportation, storage and use.

In this embodiment, the induction coil arrangement 132 has an electrically-conductive connector (not shown) that electrically connects the first flat spiral coil 31 to the second flat spiral coil 32. More specifically, the electrically-conductive connector extends from a radially-inner end 31*a* of the first flat spiral coil 31 to a radially-inner end of the second flat spiral coil 32, so as to connect the coils 31, 32 in series. In this embodiment, the electrically-conductive connector is formed as a "via" through the plate 33 of the PCB, in a way that would be understood by the person skilled in the art. In other embodiments, the electrically-conductive connector may take a different form, such as an electrically-conductive lead or wire that is internal or external to the plate 33.

In this embodiment, the flat spiral coils 31, 32 are arranged in respective substantially parallel planes. That is, each of the flat spiral coils 31, 32 has a (varying) radius that is orthogonal to the plane in which the coil 31, 32 lies. Further, the flat spiral coils 31, 32 are axially-aligned with each other. That is, the virtual point from which the path of one of the coils 31, 32 emanates lies on the same axis as the virtual point from which the path of the other of the coils 31, 32 emanates, and the axis is orthogonal to each of the respective planes in which the coils 31, 32 lie. Moreover, in this embodiment, when observed from one side of the induction coil arrangement 132, the first flat spiral coil 31 follows a clockwise path from the radially-inner end 31*a* of the first flat spiral coil 31, and the second flat spiral coil 32 follows an anti-clockwise path from the radially-inner end of the second flat spiral coil 32. In this configuration, the magnetic fields generated by the coils 31, 32 in use reinforce each other, effectively doubling the inductance of the coils 31, 32 and doubling the magnetic field along the coil axes.

As shown in FIG. 5, an aperture 333 extends fully through the plate 33 from the first side 331 of the plate 33 to the second side 332 of the plate 33. Moreover, each of the flat spiral coils 31, 32 is wound around a hole that is substantially aligned with the aperture 333 through the plate 33. That is, there is a hole at the center of each of the flat spiral coils 31, 32. Each of the aperture 333 and the holes is a through-hole. As will be described in more detail below, the heating zone 110 and the heating element 2 extend through the aperture 333 and both holes, and the varying magnetic fields generated by the coils 31, 32 in use penetrate the heating element 2.

The thickness, as measured from the first and second sides 331, 332 of the plate 33, of each of the first and second flat spiral coils 31, 32 may be, for example, greater than 50 micrometers and less than 200 micrometers, such as about 70 micrometers, about 100 micrometers or about 140 micrometers. In other embodiments, one or each of the coils 31, 32 may have a thickness less than 50 micrometers or more than 200 micrometers. The thickness chosen will help determine the resistance of the coils 31, 32 and the degree to which the coils 31, 32 self-heat in use. The thickness of the plate 33, as measured between the first and second sides 331, 332 of the plate 33, may for example be less than 2 millimeters, such as less than 1 millimeter.

While, in principle, more than two flat spiral coils could be provided in respective layers of a PCB, due to thermal conduction the outer layers of a PCB have two to three times greater current carrying capacity than any inner layers of the PCB. Accordingly, a double-coil structure such as that described above provides a balance between performance and complexity. Further, in this embodiment, each of the coils 31, 32 is a round or circular flat spiral coil. In other embodiments, one or each of the coils 31, 32 could instead be a rectangular (e.g. square) flat spiral coil. Whilst rectangular profile coils have a slightly higher inductance for a given profile, circular coils can be more easily interleaved and/or can have components packed between them, leading to an overall increase in PCB area utilization. A rectangular profile also required a longer track length for a given strength of magnetic field along the coil axis, which increases the resistance and reduces the Q value as compared to a circular coil of similar width.

The magnetic field generator 130 of this embodiment comprises first to sixth induction coil arrangements 132, each of which is identical to the induction coil arrangement 132 shown in FIG. 5 and is attached or connected to the retainer 131. In this embodiment, the retainer 131 is 3D printed SLS (selective laser sintering) nylon. In other embodiments, the retainer 131 may be formed in any other suitable way, such as from a PCB, or from any other suitable material. In some embodiments, the retainer 131 comprises a base 131 and the induction coil arrangements 132 extend away from the base 131 in a direction orthogonal or normal to a surface of the base 131.

In this embodiment, the induction coil arrangements 132 are separate components from the retainer 131, and are assembled together with the retainer 131. Each of the induction coil arrangements 132 comprises electrical connectors for both electrically connecting the coils 31, 32 to circuitry and for anchoring the induction coil arrangements 132 to the retainer 131. In other embodiments, each of the arrangements 132 may comprise electrical connectors for connecting the coils 31, 32 to circuitry, and one or more additional structural connector(s) for anchoring the induction coil arrangements 132 to the retainer 131. In still further variations to this embodiment, the retainer 131 may be integrally formed with the plates 33 (and, in some cases, also with the coils 31, 32) of the induction coil arrangements 132.

As shown in FIG. 4, the retainer 131 holds the induction coil arrangements 132 relative to one another so that the flat spiral coils 31, 32 of the induction coil arrangements 132 are arranged sequentially and in respective planes along the longitudinal axis H-H of the heating zone 110. In this embodiment, the flat spiral coils 31, 32 of the induction coil arrangements 132 lie in respective substantially parallel planes, each of which is orthogonal to the axis H-H. Further, the flat spiral coils 31, 32 are all axially-aligned with each other, since the respective virtual points from which the paths of the coils 31, 32 emanate all lie on a common axis, in this case the longitudinal axis H-H of the heating zone 110. In addition, the holes 333 through the respective plates 33 are all axially-aligned with each other, and all lie on the same axis H-H as the respective virtual points from which the paths of the coils 31, 32 emanate.

In this embodiment, the magnetic field generator 130 comprises a controller 133 for controlling operation of the flat spiral coils 31, 32. The controller 133 is housed in the retainer 131 and comprises an integrated circuit (IC), but in other embodiments the controller may take a different form. In some embodiments, the controller is for controlling operation of at least one of the flat spiral coils 31, 32 independently of at least one other of the flat spiral coils 31, 32. For example, the controller 133 may supply electrical power to the coils 31, 32 of each of the induction coil arrangements 132 independently of the coils 31, 32 of the others of the induction coil arrangements 132. In some embodiments, the controller 133 may supply electrical power to the coils 31, 32 of each of the induction coil arrangements 132 sequentially. Alternatively, in one mode of operation at least, the controller may be for controlling operation of all of the induction coil arrangements 132 simultaneously.

The retainer 131 further comprises two arms 134, 135 that extend away from the base 131 in a direction orthogonal or normal to a surface of the base 131, and substantially parallel to the induction coil arrangements 132. In this embodiment, the arms 134, 135 are 3D printed SLS (selective laser sintering) nylon and are integral with the base 131. In other embodiments, the arms 134, 135 may take a different form and may be separate components from the base 131, which are assembled together with the base 131. Each of the arms 134, 135 has an opening 134*a*, 135*a* therethrough, and the openings 134*a*, 135*a* are all axially aligned with the same axis H-H as the respective virtual points from which the paths of the coils 31, 32 emanate. In other embodiments, one or each of the arms 134, 135 may be omitted, or more than two such arms may be provided.

The apparatus 100 of this embodiment comprises a body 150 that holds the heating element 2 in position relative to the heating zone 110. A portion of the heating element 2 is outside of the heating zone 110 and embedded in the body 150. In this embodiment, the body 150 is a plug that fits into the opening 135*a* of one 135 of the arms, but in other embodiments the body 150 could take a different form. The body 150 should be made of a heat resistant material. For example, the body 150 may be made from glass or a ceramics or plastics material (such as PEEK). However, as the portion of the heating element 2 embedded in the body 150 is outside of the heating zone 110, the portion of the heating element 2 and thus the body 150 may not be substantially heated in use. The body 150 of this embodiment defines the air inlets 101 mentioned above, through which air is able to enter the heating zone 110 in use. In other embodiments, the body 150 may define only one air inlet 101 or no air inlets. In this embodiment, the heating element 2 is removable from the apparatus 100, such as for cleaning or replacement. More specifically, in this embodiment a combination of the heating element 2 and the body 150 is removable from the apparatus 100, such as by unplugging the body 150 from the opening 135*a* in the arm 135. In other embodiments, the heating element 2 may be irremovable from the apparatus 100 or removable from the apparatus 100 in a different way, such as without the body 150.

The apparatus 100 further comprises an elongate support 140 for supporting the article 10 comprising aerosolizable material in the holes in the flat spiral coils 31, 32. In this embodiment, the support 140 is tubular, encircles the heating zone 110 and has a longitudinal axis that is coaxial with the axis H-H. In some embodiments, the longitudinal axis of the support 140 may be parallel to the longitudinal axis H-H of the heating zone 110, rather than coaxial. In some embodiments, the support 140 may be non-tubular, such as rod- or pin-shaped, or have a longitudinally-extending circumferential gap therein so as to be partially or substantially tubular.

The support 140 is held in position by the arms 134, 135 and extends through the openings 134*a*, 135*a* in the arms 134, 135, through the holes in the plurality of flat spiral coils 31, 32, and through the apertures 333 in the plates 33. In this embodiment, the elongate support 140 is magnetically impermeable and electrically non-conductive, so as not to interfere with the varying magnetic fields generated by the coils 31, 32 in use. The elongate support 140 may, for example, be made from glass or a ceramics or plastics material (such as PEEK). However, in some embodiments, the elongate support 140 may be magnetically permeable and/or electrically conductive, and may be heated in use by penetration with the varying magnetic fields so as to aid heating of the heating zone 110 and the article 10 therein in use. In still further embodiments, the elongate support 140 may be omitted.

The magnetic field generator 130 also comprises an electrical power source (not shown), and a user interface (not shown) for user-operation of the controller 133. In this embodiment, the electrical power source is a rechargeable battery. In other embodiments, the electrical power source may be other than a rechargeable battery, such as a non-rechargeable battery, a capacitor or a connection to a mains electricity supply.

The controller 133 is electrically connected between the electrical power source and the coils 31, 32 of the induction coil arrangements 132, and is communicatively connected to the user interface, which may be located at the exterior of the apparatus 100. The controller 133 is operated in this embodiment by user-operation of the user interface. The user interface may comprise a push-button, a toggle switch, a dial, a touchscreen, or the like.

In this embodiment, operation of the user interface by a user causes the controller 133 to cause an alternating electrical current to pass through one or more of the coils 31, 32 of the induction coil arrangements 132, so as to cause the or each coil 31, 32 to generate an alternating magnetic field. The coils 31, 32 and the heating element 2 are relatively positioned so that the alternating magnetic field(s) produced by the coil(s) 31, 32 penetrate(s) the heating material of the heating element 2. When the heating material of the heating element 2 is an electrically-conductive material, this may cause the generation of one or more eddy currents in the heating material. The flow of eddy currents in the heating material against the electrical resistance of the heating material causes the heating material to be heated by Joule heating. Further, when the heating material of the heating element 2 is a magnetic material, the orientation of magnetic dipoles in the heating material changes with the changing applied magnetic field, which causes heat to be generated in the heating material.

In this embodiment, the article 10 is elongate with a longitudinal axis C-C. When the article 10 is located in the heating zone 110 in use, this axis C-C lies coaxial with, or parallel to, the longitudinal axis H-H of the heating zone 110. Accordingly, the heating of one of more portion(s) 21, 22, 23, 24, 25, 26 of the heating element 2 causes heating of one or more corresponding portion(s) of the heating zone 110, and heating of one of more corresponding section(s) 12*a*, 12*b*, 12*c*, 12*d*, 12*e*, 12*f* of the aerosolizable material 12 of the article 10 when the article 10 is located in the heating zone 110.

In some embodiments, the controller 133 is operable to cause heating of a first section of the aerosolizable material 12 before heating of a second section of the aerosolizable material 12. That is, the controller 133 may be operable to cause a varying electrical current to pass through one or both of the coils 31, 32 of a first of the induction coil arrangements 132 to initiate volatilization of at least one component of a first section 12*a* of the aerosolizable material 12 adjacent the first induction coil arrangement and formation of an aerosol therein, before causing a varying electrical current to pass through one or both of the coils 31, 32 of a second of the induction coil arrangements 132 to initiate volatilization of at least one component of a second section 12*b* of the aerosolizable material 12 adjacent the second induction coil arrangement 132 and formation of an aerosol therein. Accordingly, there may be provided progressive heating of the aerosolizable material 12 of the article 10 over time.

In some embodiments, the first induction coil arrangement 132 and associated first section 12*a* of the aerosolizable material 12 may be those nearest the first end 111 of the heating zone 110, and the second induction coil arrangement 132 and associated second section 12*b* of the aerosolizable material 12 may be closer to the second end 112 of the heating zone 110. This helps to enable an aerosol to be formed and released relatively rapidly from the article 10 at the first section 12*a* of the aerosolizable material 12 relatively close to the outlet 102, for inhalation by a user, yet provides time-dependent release of aerosol, so that aerosol continues to be formed and released even after the first section 12*a* of the aerosolizable material 12 has ceased generating aerosol. Such cessation of aerosol generation may occur as a result of the first section 12*a* of the aerosolizable material 12 becoming exhausted of volatilizable components.

The apparatus 100 may comprise a temperature sensor (not shown) for sensing a temperature of the heating zone 110 or of the article 10 or of the heating element 2. The temperature sensor may be communicatively connected to the controller 133, so that the controller 133 is able to monitor the temperature. On the basis of one or more signals received from the temperature sensor, the controller 133 may adjust a characteristic of the varying or alternating electrical current passed through the coils 31, 32 as necessary, in order to ensure that the temperature of the aerosolizable material 12 remains within a predetermined temperature range. The characteristic may be, for example, amplitude or frequency or duty cycle. Within the predetermined temperature range, in use the aerosolizable material 12 is heated sufficiently to volatilize at least one component of the aerosolizable material 12 without combusting the aerosolizable material 12. Accordingly, the controller 133, and the apparatus 100 as a whole, is arranged to heat the aerosolizable material 12 to volatilize the at least one component of the aerosolizable material 12 without combusting the aerosolizable material 12.

In some embodiments, the temperature range is about 150° C. to about 300° C. The temperature range may be greater than 150° C., or greater than 200° C., or greater than 250° C., for example. The temperature range may be less than 300° C., or less than 290° C., or less than 250° C., for example. In some embodiments, the upper limit of the temperature range could be greater than 300° C. In some embodiments, the temperature sensor may be omitted.

In variations to this embodiment, the heating element 2 may be penetrable by fewer than all of the varying magnetic fields in use. In some such variations, the non-penetrated portion(s) of the heating element 2 may be heated in use by thermal conduction from the penetrated portion(s) of the heating element 2.

In some embodiments, the article 10 may include at least one heating element comprising heating material that is heatable in use by penetration with one or more of the varying magnetic fields to heat the aerosolizable material 12 of the article 10. The heating element(s) of the article 10 would be in thermal contact, and in some embodiments surface contact, with the aerosolizable material 12 of the article 10. For example, a heating element of such an article 10 may be elongate and extend from a first end of the article 10 to an opposite second end of the article 10. The heating element of the article 10 may be tubular or rod-shaped, for example. In some such embodiments, the aerosolizable material may be radially inwards or radially outwards of the tubular heating element of the article 10. In some embodiments, the article 10 may include heating material that is dispersed within the aerosolizable material 12 of the article 10. For example, the article 10 may include a material comprising a mixture of aerosolizable material 12 and elements, wherein each of the elements comprises heating material that is heatable by penetration with a varying magnetic field. Each of the elements may comprise a closed circuit of heating material. Some or each of the elements may be ring-shaped, spherical, or formed from a plurality of discrete strands of heating material, for example.

In some embodiments, the apparatus 100 is sold, supplied or otherwise provided separately from the article 10 with which the apparatus 100 is usable. However, in some embodiments, the apparatus 100 and one or more of the articles 10 may be provided together as a system, such as a kit or an assembly, possibly with additional components, such as cleaning utensils.

In each of the above described embodiments, the article 10 is a consumable article. Once all, or substantially all, of the volatilizable component(s) of the aerosolizable material 12 in the article 10 has/have been spent, the user may remove the article 10 from the heating zone 110 of the apparatus 100 and dispose of the article 10. The user may subsequently re-use the apparatus 100 with another of the articles 10. However, in other respective embodiments, the article may be non-consumable, and the apparatus and the article may be disposed of together once the volatilizable component(s) of the aerosolizable material has/have been spent.

In each of the embodiments discussed above the heating material is stainless steel. However, in other embodiments, the heating material may comprise one or more materials selected from the group consisting of: an electrically-conductive material, a magnetic material, and a magnetic electrically-conductive material. In some embodiments, the heating material may comprise a metal or a metal alloy. In some embodiments, the heating material may comprise one or more materials selected from the group consisting of: aluminum, gold, iron, nickel, cobalt, conductive carbon, graphite, steel, plain-carbon steel, mild steel, stainless steel, ferritic stainless steel, copper, and bronze. Other heating material(s) may be used in other embodiments.

In each of the above described embodiments, the aerosolizable material comprises tobacco. However, in respective variations to each of these embodiments, the aerosolizable material may consist of tobacco, may consist substantially entirely of tobacco, may comprise tobacco and aerosolizable material other than tobacco, may comprise aerosolizable material other than tobacco, or may be free from tobacco. In some embodiments, the aerosolizable material may comprise a vapor or aerosol forming agent or a humectant, such as glycerol, propylene glycol, triacetin, or diethylene glycol.

In order to address various issues and advance the art, the entirety of this disclosure shows by way of illustration and example various embodiments in which the claimed invention may be practiced and which provide for superior tubular heating elements, apparatus for heating aerosolizable material to volatilize at least one component of the aerosolizable material, and systems comprising such apparatus and an article comprising aerosolizable material. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. A tubular heating element for use in an apparatus for heating aerosolizable material to volatilize at least one component of the aerosolizable material, the tubular heating element comprising:

heating material that is heatable by penetration with a varying magnetic field, and wherein the tubular heating element has a wall thickness of no more than 1 millimeter.

2. The tubular heating element of claim 1, wherein the wall thickness is no more than 0.3 millimeters.

3. The tubular heating element of claim 1, wherein an outside diameter or dimension of the tubular heating element is between 0.3 millimeters and 5 millimeters.

4. The tubular heating element of claim 1, comprising a heat resistant support and a coating on the heat resistant support, wherein the coating comprises the heating material.

5. The tubular heating element of claim 4, wherein the coating is located radially outwards of the heat resistant support.

6. A tubular heating element for use in an apparatus for heating aerosolizable material to volatilize at least one component of the aerosolizable material, the tubular heating element comprising:

a heat resistant support; and a coating on the heat resistant support, wherein the coating comprises heating material that is heatable by penetration with a varying magnetic field, and wherein the coating is located radially outwards of the heat resistant support.

7. The tubular heating element of claim 6, wherein the heating material of the coating is a ferromagnetic material.

8. The tubular heating element of claim 6, comprising a heat resistant protective coating, wherein the coating comprising the heating material is located between the heat resistant support and the heat resistant protective coating.

9. An apparatus for heating aerosolizable material to volatilize at least one component of the aerosolizable material, the apparatus comprising:

a heating zone for receiving one or more articles comprising aerosolizable material;

a heating element comprising heating material that is heatable by penetration with a varying magnetic field to heat the heating zone, wherein the heating element is encircled by the heating zone; and a magnetic field generator for generating varying magnetic fields that penetrate respective longitudinal portions of the heating element in use, wherein the magnetic field generator comprises a plurality of flat spiral coils of electrically-conductive material arranged sequentially and in respective planes along a longitudinal axis of the heating zone.

10. The apparatus of claim 9, wherein the heating element extends parallel to, or coaxially with, the longitudinal axis of the heating zone.

11. The apparatus of claim 9, wherein the heating element is tubular.

12. The apparatus of claim 9, wherein the heating element comprises a heat resistant support and a coating on the heat resistant support, wherein the coating comprises the heating material.

13. The apparatus of claim 12, wherein the heating material of the coating is a ferromagnetic material.

14. The apparatus of claim 9, wherein the heating element is a tubular heating element comprising:

a heat resistant support, and a coating on the heat resistant support, wherein the coating comprises heating material that is heatable by penetration with a varying magnetic field, and wherein the coating is located radially outwards of the heat resistant support.

15. The apparatus of claim 9, wherein the planes are substantially parallel to one another.

16. The apparatus of claim 9, wherein the heating zone extends through a hole in each of the plurality of flat spiral coils.

17. The apparatus of claim 16, comprising an elongate support for supporting an article comprising aerosolizable material in the holes in the plurality of flat spiral coils.

18. The apparatus of claim 17, wherein the elongate support is at least one of magnetically impermeable or electrically non-conductive.

19. The apparatus of claim 9, wherein the apparatus is a tobacco heating product.

20. A system for heating aerosolizable material to volatilize at least one component of the aerosolizable material, the system comprising:

the apparatus according to claim 9; and the one or more articles comprising aerosolizable material and for locating in the heating zone of the apparatus.

* * * * *